United States Patent [19]

Rozen et al.

[11] Patent Number: 4,973,774

[45] Date of Patent: Nov. 27, 1990

[54] CHLOROFLUOROHYDROCARBON PURIFICATION PROCESS

[75] Inventors: Shlomo M. Rozen; Bruce E. Smart, both of Wilmington, Del.

[73] Assignee: E. I. Du Pont de Nemours and Company, Wilmington, Del.

[21] Appl. No.: 430,945

[22] Filed: Nov. 2, 1989

[51] Int. Cl.$^5$ ............................................. C07C 17/38
[52] U.S. Cl. ...................................... 570/178; 570/177
[58] Field of Search ........................ 570/177, 179, 178

[56] References Cited

U.S. PATENT DOCUMENTS

| | | | |
|---|---|---|---|
| 3,321,383 | 5/1967 | Scherer et al. | 203/37 |
| 3,391,201 | 7/1968 | Jaeger | 570/179 |
| 4,766,261 | 8/1988 | Bierl | 570/179 |

FOREIGN PATENT DOCUMENTS 0002098  5/1979  European Pat. Off. ............ 570/177

Primary Examiner—Alan Siegel

[57] ABSTRACT

Chlorofluorohydrocarbons contaminated with unwanted isomers during the process for their manufacture are purified by reacting the mixture with alcohol solutions of alkali metal and then separating the ether derivatives of the isomers from the mixture.

4 Claims, No Drawings

CHLOROFLUOROHYDROCARBON PURIFICATION PROCESS

BACKGROUND OF THE INVENTION

This invention relates to a process for the purification of chlorofluorohydrocarbons and particularly to the removal of 1,2-dichloro-1,1-difluoroethane from 1,1-dichloro-1,2-difluoroethane.

Many chlorofluorohydrocarbons which are being considered as environmentally safe replacements are produced in processes wherein the desired product is contaminated with unwanted isomers, which in some instances, e.g., 1,2-dichloro-1,1-difluoroethane (HCFC-132b), may be toxic. Often when a mixture of isomers is obtained, separation into its components by distillation is extremely difficult due to the similarity of the isomer boiling points. For example, 1,1-dichloro-1,2-difluoroethane (HCFC-132c) boils at 50° C. while its isomer HCFC-132b boils at 47° C.

It is therefore an object of the present invention to provide a process for the separation of unwanted isomers produced during the manufacture of chlorofluorohydrocarbons.

SUMMARY OF THE INVENTION

This invention provides a process tracking a mixture for the removal of compounds of the following formula:

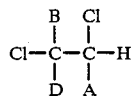
    I where A equals H, Cl, or an alkyl group of the formula $C_mH_nX_p$ where X is chlorine and/or fluorine, m is 1 to 4, and n and p are 0 to 9; B and D are H, Cl, or F; by reacting the mixture with alcohol solutions of alkali metal and then separating the ether derivatives of compounds of formula I from the reaction mixture.

DETAILS OF THE INVENTION

A mixture of compounds containing moieties of empirical formula I can be purified, i.e., compounds of empirical formula I removed, by treating such mixtures with alcoholic bases and converting compounds of empirical formula I to their ether deriviatives. These ethers are easily separated from the desired compound by distillation since the ether boiling points are much higher. For example we have discovered that treating a mixture of HCFC-132c and HCFC-132b prepared by the addition of fluorine to 1,1,-dichloro-ethylene as disclosed in U.S. Pat. No. 4,754,085, with alcoholic bases converts the HCFC-132b to the ether written below.

    II where M is Li, Na, K, Rb or Cs, and where ROH is a $C_1$ to $C_6$ primary alcohol. Preferably the base is NaOH because of convenience and its solubility and the preferred alcohol is n-butanol because of the boiling point difference of the n-butyl ether derivative and the desired compound(s). The reaction rate is determined by the temperature. Thus, at room temperature HCFC-132b completely disappears after 6 hours but at 50° C. (the reflux temperature of HCFC-132c) the reaction is over after 5 minutes. It should be noted that FC-132c is completely inert to the employed basic conditions even after prolonged periods, e.g., five hours at boiling n-butanol temperature.

The reaction for the removal of compounds of formula I from reaction mixtures containing them can be run at both atmospheric and superatmospheric pressure.

At least 2 mole equivalents of base (based on the amount of HCFC-132b) should be present. The described treatment can also be carried in the presence of large amounts of $CCl_3F$, e.g., which is present in the mixture as an unreacted material or by-product. If however, the base treatment is performed on the crude reaction mixture, more base should be present since there might be additional minor by-products which would consume part of it.

The process will be further illustrated by the following Examples.

EXAMPLES General Procedure

GC analyses were usually run on a 2' Supelco 20% FS® 1265 polysilicone column. GC/MS and GC/IR were run using a Supelco 5% Krytox® perfluorinated polyether column. $^{19}F$ NMR of HCFC-132b: $-59.2$ ppm (t, J=11 Hz); $^1H$ NMR: 4.01 ppm (t, J=11 Hz); $^{19}F$ NMR of HCFC-132c: $-67.0$ (1F, dt, $J_1=14$ Hz, $J_2=23$ Hz), 210.2 ppm (1F, dt, $J_1=47$ Hz, $J_2=23$ Hz); $^1H$ NMR: 4.7 ppm (dd, $J_1=47$ Hz, $J_2=14$ Hz).

EXAMPLE 1

$CCl_2FCH_2F$ Purification $CCl_2FCH_2F$, HCFC-132c (21 mL, 30 g), containing about 2% $CClF_2CH_2Cl$, HCFC-132b, was stirred at room temperature with a solution made from NaOH (350 mg) and EtOH (8 mL). After 30 minutes most of the HCFC-132b was still present. After 4 hours 60% of the HCFC-132b had disappeared and after 5.5 hours no traces of it were detected. The reaction mixture was poured into ice-cold water (20 mL) and the organic layer (19 mL) was separated and dried over $MgSO_4$. Besides the peaks of the major component, the following signals were also detected: $^{19}F$ NMR: $-79.33$ ppm (t, J=8.5 Hz); $^1H$ NMR: 3.95 (2H, q, J=6.4 Hz), 3.7 (2H, t, J=8 Hz) and 1.3 ppm (3H, t, 6.4 Hz).

These spectra are in excellent agreement with the suggested compound resulting from the reaction between HCFC-132b and EtOH/NaOH namely, $EtOCF_2CH_2Cl$. Distillation afforded HCFC-132c with purity higher than 99.95%.

EXAMPLE 2

$CCl_2FCH_2F$ Purification

HCFC-132c (20 g) containing 2% HCFC-132b was stirred overnight with MeOH (8 mL) containing NaOH (400 mg). The reaction mixture was worked up as in Example 1. No HCFC-132b was detected by $^1H$ and $^{19}F$ NMR. These spectra showed that HCFC-132b was converted to $MeOCF_2CH_2Cl$: $^{19}F$ NMR: $-82.2$ ppm (t, J=8 Hz); $^1H$ NMR: 3.7 (2H, t, J=8 Hz), 2.35 ppm (3H, s). Distillation afforded HCFC-132c (16.5g) of greater than 99.5% purity containing less than 250 ppm of HCFC-132b.

EXAMPLE 3

CCl$_2$FCH$_2$F Purification

HCFC-132c (19.7 g) containing about 2% HCFC-132b was treated with n-BuOH (10 mL) containing NaOH (0.4 g). The reaction mixture was stirred overnight at room temperature and worked up as in Example 1. Distillation afforded HCFC-132c (>15 g) of greater than 99.5% purity containing less than 250 ppm of HCFC-132b.

EXAMPLE 4

CCl$_2$FCH$_2$F Purification

HCFC-132c (20 mL) containing HCFC-132b (0.4 mL) was treated with a solution of NaOH (0.4 g) in n-BuOH (20 mL). After 5 minutes at reflux, the reaction mixture was added to 50 mL ice cold water (50 mL), the organic layer separated, washed again with cold water and dried over MgSO$_4$. Organic material (19 mL) was obtained of which 98% proved to be HCFC-132c The remaining 2% was identified as the corresponding ether: n-BuOCF$_2$CH$_2$Cl which was easily separated by distillation. The purity of the HCFC-132c was confirmed by GC/MS, GC/IR, $^{19}$F NMR and $^1$H NMR. No change of the HCFC-132C was detected after refluxing with NaOH/n-BuOH for several hours.

What is claimed is:

1. A process for the separation of a compound of the formula:

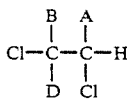

wherein
A is Cl, H or $C_mH_nX_p$ where X is chlorine or fluorine; m is 1 to 4, n is 0 to 9 and p is 0 to 9;
B is Cl, F or H; or
D is Cl, F or H;
from a reaction mixture of said compounds of FCH$_2$—CCl$_2$F, comprising contacting the mixture with at least two mole equivalents of alcoholic base per mole of compound, having an alcohol of the formula ROH and a base of the formula MOH the formula:

MOH/ROH wherein
M is Na, Li, K, Rb or Cs; and
R is alkyl of 1-6 carbons at a temperature between 20° C. and the boiling point of the mixture for a period of time sufficient to convert the compound to an ether of the formula:

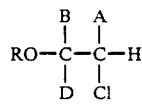

wherein:
A, B, D and R are as defined, and separating the ether from the mixture.

2. A process for the separation of F$_2$ClC—CH$_2$Cl from a mixture of F$_2$ClC—CH$_2$Cl and FCH$_2$—CCl$_2$F comprising contacting the mixture with at least two mole equivalents of an alcoholic base per mole of F$_2$ClC—CH$_2$Cl, the alcoholic base having an alcohol of the formula ROH and a base of the formula MOH the formula:

MOH/ROH wherein
M is Na, Li, K, Rb or Cs; and
R is alkyl of 1-6 carbons at a temperature between 20° C. and 50° C. for a period of time sufficient to convert the F$_2$ClC—CH$_2$Cl to RO—F$_2$C—CH$_2$Cl and separating the RO—F$_2$C—CH$_2$Cl from the mixture.

3. The process of claims 1 or 2 wherein M is Na and R is n-butyl.

4. The process of claims 1 and 2 wherein the ether is separated from the mixture by distillation.

* * * * *